(12) United States Patent
Wei

(10) Patent No.: US 10,661,020 B2
(45) Date of Patent: May 26, 2020

(54) MEDICATION DELIVERY DEVICE

(71) Applicant: Min Wei, Carmel, IN (US)

(72) Inventor: Min Wei, Carmel, IN (US)

(73) Assignee: Min Wei, Carmel, IN (US)

( * ) Notice: Subject to any disclaimer, the term of this patent is extended or adjusted under 35 U.S.C. 154(b) by 382 days.

(21) Appl. No.: 15/126,658

(22) PCT Filed: Apr. 8, 2015

(86) PCT No.: PCT/US2015/024998
§ 371 (c)(1),
(2) Date: Sep. 16, 2016

(87) PCT Pub. No.: WO2015/160600
PCT Pub. Date: Oct. 22, 2015

(65) Prior Publication Data
US 2017/0080159 A1     Mar. 23, 2017

Related U.S. Application Data

(60) Provisional application No. 61/979,996, filed on Apr. 15, 2014.

(51) Int. Cl.
*A61M 5/315* (2006.01)
*A61M 5/32* (2006.01)
*A61M 5/31* (2006.01)
*A61M 5/20* (2006.01)

(52) U.S. Cl.
CPC ...... *A61M 5/31515* (2013.01); *A61M 5/2033* (2013.01); *A61M 5/3137* (2013.01); *A61M 5/31501* (2013.01); *A61M 5/3204* (2013.01); *A61M 2005/206* (2013.01); *A61M 2005/3139* (2013.01); *A61M 2005/31508* (2013.01)

(58) Field of Classification Search
CPC ........ A61M 5/3137; A61M 2005/3139; A61M 5/31511; A61M 5/3158; A61M 5/31581; A61M 5/3204; A61M 5/2033
See application file for complete search history.

(56) References Cited

U.S. PATENT DOCUMENTS

| 6,203,530 B1* | 3/2001 | Stewart, Sr. | A61M 5/2033 604/207 |
| 8,021,335 B2* | 9/2011 | Lesch, Jr. | A61M 5/2033 604/135 |
| 8,915,886 B2* | 12/2014 | Cowe | A61M 5/31511 604/187 |
| 9,750,885 B2* | 9/2017 | Weaver | A61M 5/31513 |
| 2005/0192530 A1* | 9/2005 | Castellano | A61M 5/30 604/70 |
| 2010/0049125 A1* | 2/2010 | James | A61M 5/2033 604/110 |

* cited by examiner

*Primary Examiner* — Matthew F Desanto
(74) *Attorney, Agent, or Firm* — Min Wei

(57) ABSTRACT

A mechanical device for assisting medication injection is provided herein comprising a connector having a distal end and a proximal end; a piston rod locked in said connector before medication injection; a spring configured to bias said piston rod distally; a releasable restraining means configured to releasably restrain said piston rod in a locked state against said biasing of said spring, wherein, upon release of said releasable restraining means, said piston rod moves distally under force of said spring; an activation means configured to release said releasable restraining means; and a mounting means for mounting a syringe at said distal end of said connector.

8 Claims, 11 Drawing Sheets

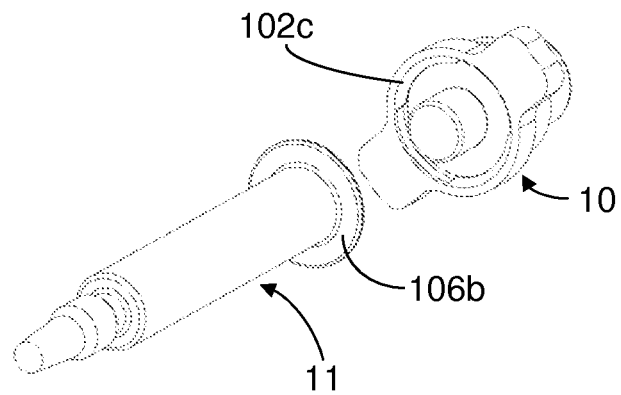
FIG. 5
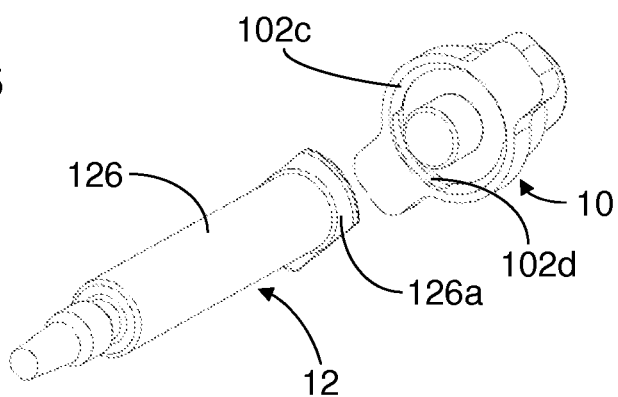
FIG. 6
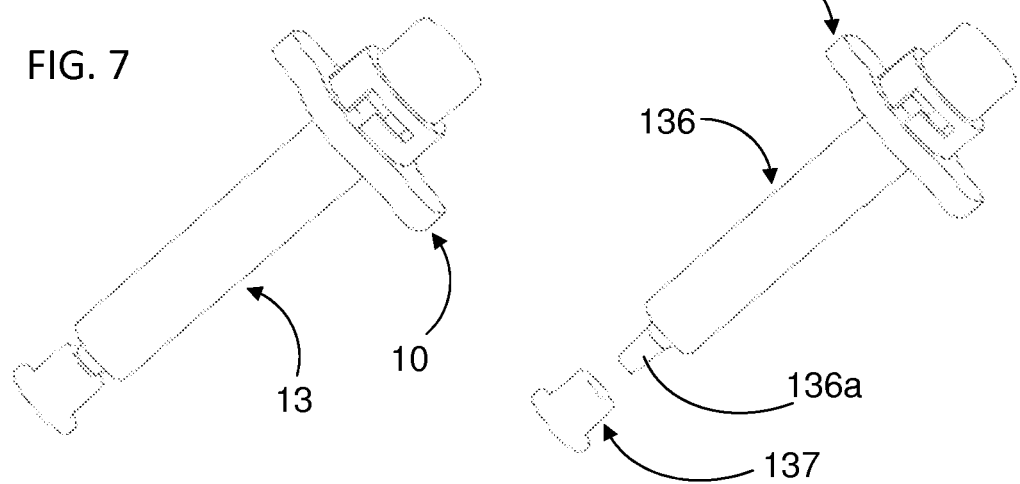
FIG. 7
FIG. 7A

MEDICATION DELIVERY DEVICE

TECHNICAL FIELD

The invention relates to an automatic injection device for delivering liquid medications in a syringe or similar format.

BACKGROUND OF THE INVENTION

As the parenteral drugs become more and more popular, medication injection devices are expected to be widely used. Pre-filled syringe and patient self-use autoinjector are the current forms of medication injection devices used for delivering parenteral drugs. Examples of pre-filled syringe can be found in U.S. Pat. Nos. 6,189,292 and 7,428,807. Examples of autoinjector device can be found in U.S. Pat. Nos. 7,794,432 and 8,808,250. Using pre-filled syringe and autoinjector device can ease medication preparation/administration procedure and reduce needle injury, which results in improved patient convenience and compliance. There are a number of mechanical autoinjector devices designed for patient self-injection. However, there is no mechanical assisting medication delivery device designed for health care professionals who deliver medication to patients. This gap lead to following issues for health care professionals—
a. Without mechanical assisting mechanism, manual pre-filled syringe is not ergonomic for multiple injections in a repetitive manner, which is often the case for healthcare professionals.
b. For medication formulation with high viscosity and high delivery volume, it requires extra finger force for successful delivery using the manual pre-filled syringe. This is not optimal for healthcare professionals.
c. The current mechanical autoinjector devices are designed based on the human factor needs for patient self-injection. Therefore, the designs are often inconvenient for healthcare professional to use, from the human factor point of view.

Furthermore, the sizes of current mechanical autoinjector devices are large, which is unnecessary for most hospital setting and waste materials for single injection. Therefore, injection devices based on a novel design principal are in need.

SUMMARY OF THE INVENTION

It is an object of the present invention to provide a mechanical device for medication injection. This invention presents a series of the designs for devices assisting medication injection comprising: 1) a user triggered activation mechanism; 2) a spring force driven piston rod; and 3) a mounting mechanism for mounting a syringe on the devices. It is an advantage of the present invention that the injection assisting device embodiments here can be kept separately from syringe before use, as a universal injection assisting apparatus for syringes, especially for pre-filled syringes filled with different medications. It is also an advantage of the present invention that the injection assisting device embodiments here have a short piston push rod. Therefore, the overall size of the device is significantly smaller and the storage space of the device can be greatly reduced. It is a further advantage of the present invention that the target users of the device designs are medical professionals.

BRIEF DESCRIPTION OF THE DRAWINGS

The figures are schematic and simplified for clarity, and they just show details, which are essential to the understanding of the invention, while other details are left out. Throughout, the same reference numerals are used for identical or corresponding parts.

FIG. 5 shows the mounting of a pre-filled syringe having staked-needle and round syringe barrel flange on the exemplary injection assisting device according to the invention.

FIG. 6 shows the mounting of a pre-filled syringe having staked-needle and cut syringe barrel flange on the exemplary injection assisting device according to the invention.

FIG. 7 and FIG. 7A show the exemplary injection assisting device assembled together with a pre-filled syringe having luer taper fitting according to the invention.

Corresponding parts are marked with the same reference symbols in all figures.

DETAILED DESCRIPTION THE DRAWINGS

Figure 1:
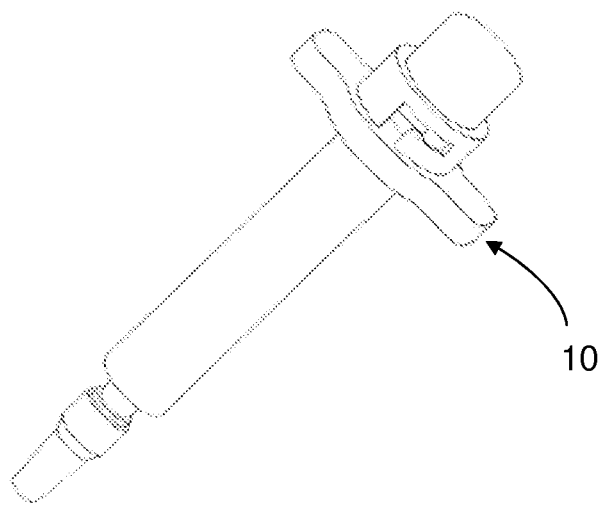
FIG. 1 is a perspective view of an exemplary injection assisting device assembled together with a pre-filled syringe having staked-needle according to the invention.
Figure 2:
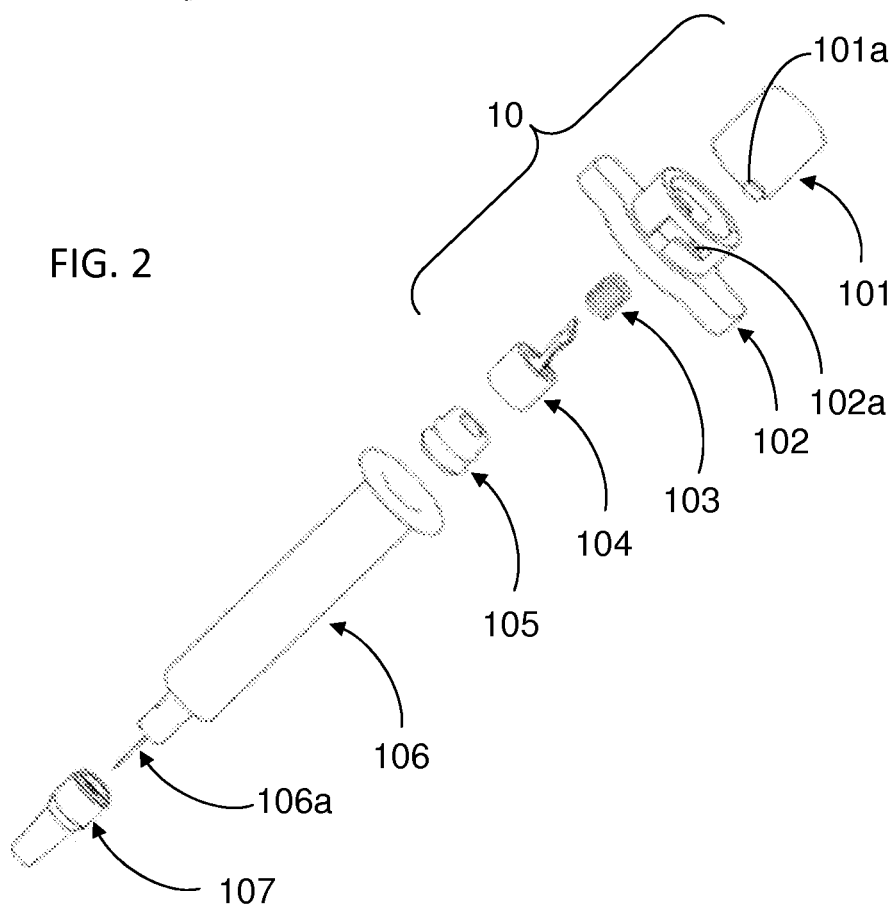
FIG. 2 is an exploded view of the exemplary injection assisting device assembled together with a pre-filled syringe having staked-needle according to the invention.

The present invention will become more fully understood from the detailed description given hereinbelow and the accompanying drawings which are given by way of illustration only, and thus, are not limitive of the present invention, and wherein:

The apparatus and methods presented herein can be used for injecting any of a variety suitable therapeutic agents or substances, such as a drug, into a patient. Initially it may be convenient to define that, the term "distal end" is meant to refer to the end of the apparatus close to the injection site, whereas the term "proximal end" is meant to refer to the end opposite to the "distal end" along the longitudinal axis of the device body. The words "upper", "lower", "up", "down", "right" and "left" designate directions in the drawings to which reference is made. The words "inward" and "outward" refer to directions toward and away from, respectively.

Figure 3:
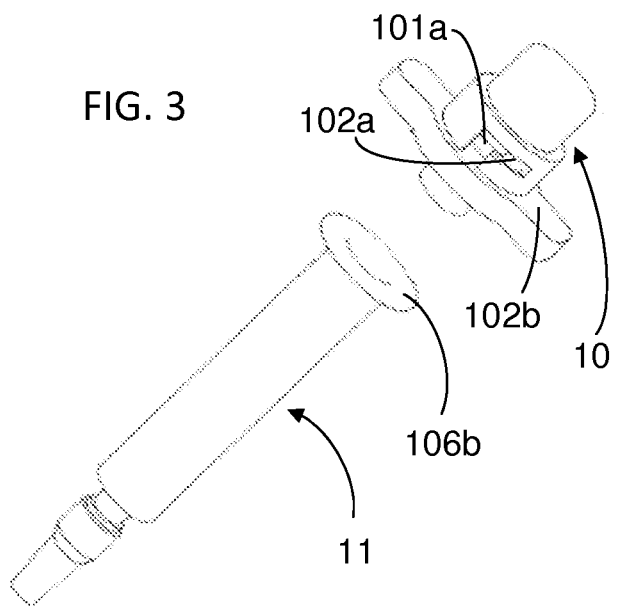
FIG. 3 is another exploded view of the assembling between the exemplary injection assisting device and a pre-filled syringe having staked-needle according to the invention.
Figure 3A:
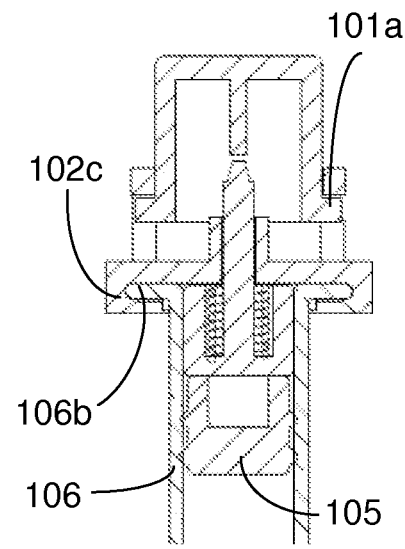
FIG. 3A is a cross-sectional view showing the mounting a pre-filled syringe having staked-needle on the exemplary injection assisting device according to the invention.
Figure 4:
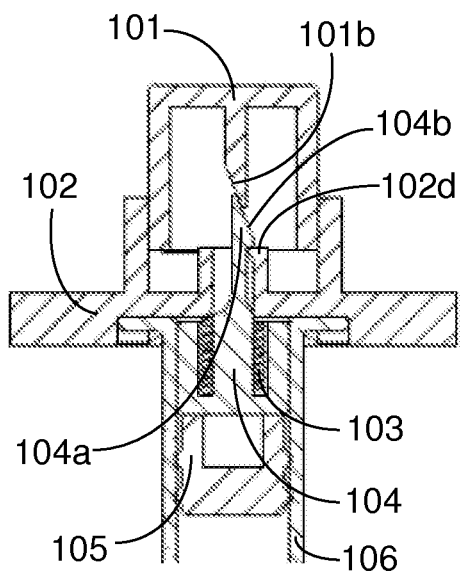
FIG. 4 shows a series of cross-sectional views of the activation of the exemplary injection assisting device assembled together with a pre-filled syringe having staked-needle according to the invention.
Figure 4:
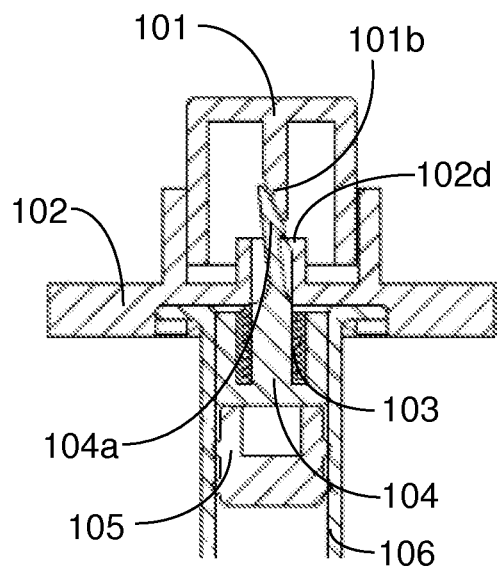
Figure 8:
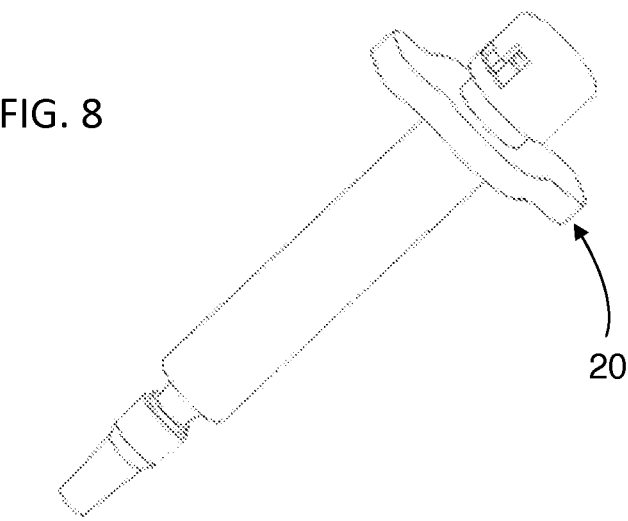
FIG. 8 is a perspective view of the first alternative injection assisting device assembled together with a pre-filled syringe having staked-needle according to the invention.
Figure 9:
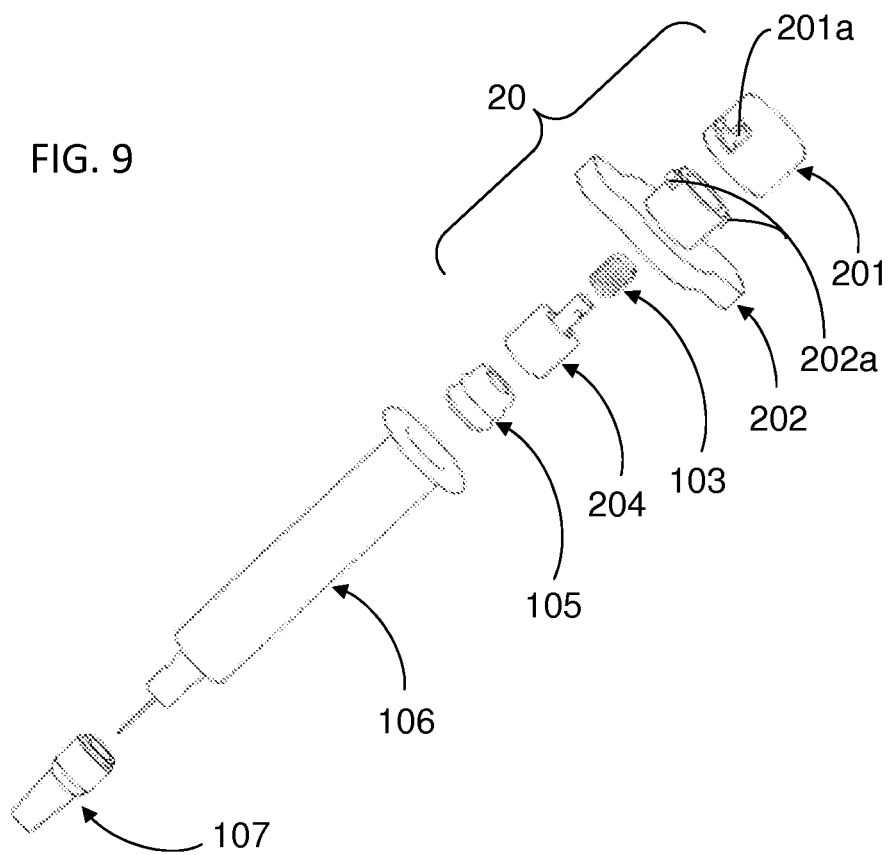
FIG. 9 is an exploded view of the first alternative injection assisting device assembled together with a pre-filled syringe having staked-needle according to the invention.

FIGS. 1-7A illustrate the construction and function mechanism of an exemplary injection assisting device assembly 10 according to the invention. In this exemplary injection assisting device assembly 10, a push cap 101 is used to activate an automatic injection. The push cap 101 is engaged with a connector 102, through guide keys 101a provided on the push cap 101 and tracks 102a being defined on the connector 102. This engagement prevents incidental activation of the device before use. During use, the push cap 101 is rotated to an activation position so that the push cap 101 can be pushed toward distal end of the device. Wing-shape feature 102b on the connector 102 is for finger gripping. FIGS. 3 and 3A show the mounting a pre-filled syringe onto the exemplary injection assisting device assembly 10. The pre-filled syringe 11 has a syringe barrel 106 with a staked needle 106a and a needle shield 107. The connection between the exemplary injection assisting device assembly 10 and the pre-filled syringe 11 is formed through snap-fit features 102c at the distal end of the connector 102 and a round flange feature 106b on the pre-filled syringe barrel 106. A latch lock mechanism is formed between a piston rod 104 and the connector 102. With reference to FIG. 4, the injection assisting device assembly 10 is shown with the piston rod 104 in a locked state. The piston rod 104 is restrained in the locked state, against biasing force of a spring 103, by a deflectable latch formed between a feature 104a on the piston rod 104 and a feature 102d on the connector 102. The interengagement of the feature 104a on the piston rod 104 and the feature 102d on the connector 102 restricts distal movement of the piston rod 104 under the biasing force of the spring 103. Upon activation, the push cap 101 is pushed toward the distal end of the device, a distally-directed chamfered actuation surface 101b on the push cap 101 engages with a chamfered engagement surface 104b on the piston rod 104 and push the restraining feature 104a on the piston rod 104 to bend toward left and away from the feature 102d on the connector 102. Then, the latch lock mechanism formed between the piston rod 104 and the connector 102 is released and the spring 103 drives the piston rod 104 to move toward the distal end of the pre-filled syringe 11. The piston rod 104 pushes a piston 105 inside the pre-filled syringe 11 move toward the distal end of the pre-filled syringe 11. As the result, medication filled in the pre-filled syringe 11 is injected. FIG. 5 shows the snap-fit feature 102c on the connector 102 and a round flange 106b on the pre-filled syringe barrel 106. To mount the pre-filled syringe 11 on the exemplary injection assisting device assembly 10, the two sub-assemblies, 10 and 11, are snapped together along the axial direction of the device. FIG. 6 shows a connection between the exemplary injection assisting device assembly 10 and a pre-filled syringe 12 with a cut flange 126a on a syringe barrel 126. To mount the pre-filled syringe 12 on the exemplary injection assisting device assembly 10, the cut flange 126a is first inserted into opening slots 102d on the connector 102, then the syringe barrel 126 is rotated so that the cut flange 126a is locked in the snap features 102c at the distal end of the connector 102. FIGS. 7 and 7A show the exemplary injection assisting device assembly 10 assembled together with a pre-filled syringe 13 having luer taper fitting. The pre-filled syringe 13 has a syringe barrel 136 with luer taper fitting 136a and a tip cap 137 for sealing the medication inside the pre-filled syringe 13.

Figure 10:
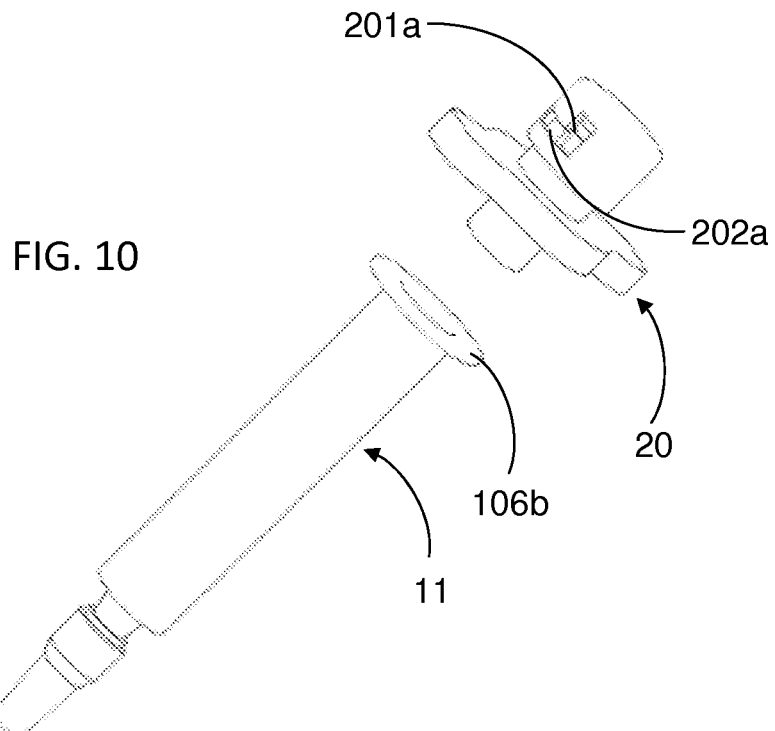
FIG. 10 is another exploded view of the assembling between the first alternative injection assisting device and a pre-filled syringe having staked-needle according to the invention.
Figure 11:
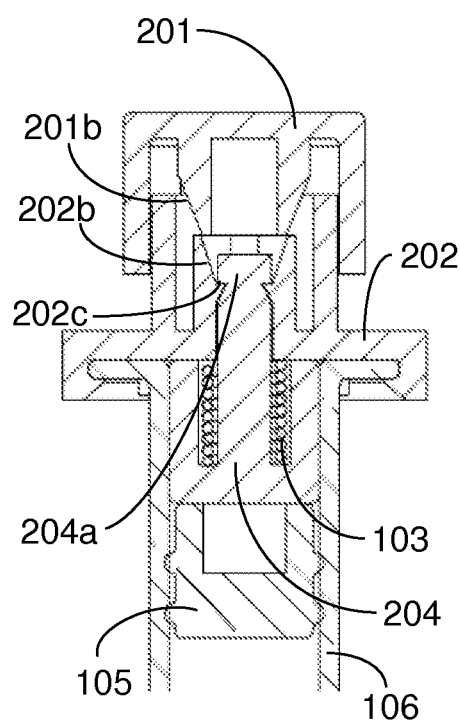
FIG. 11 shows a series of cross-sectional views of the activation the first alternative injection assisting device assembled together with a pre-filled syringe having staked-needle according to the invention.
Figure 11:
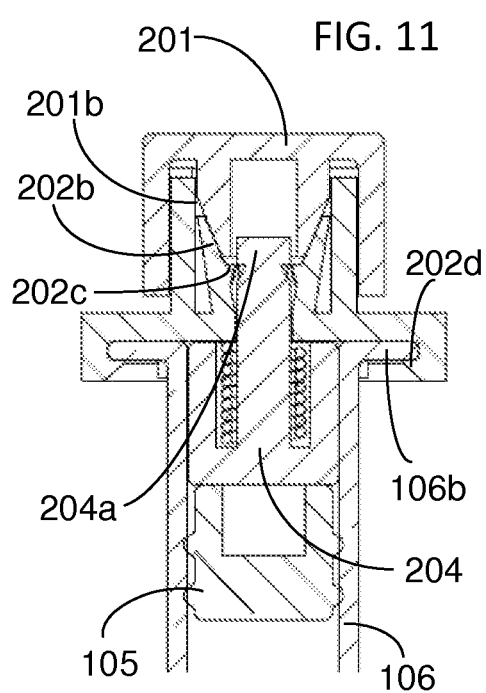
Figure 12:
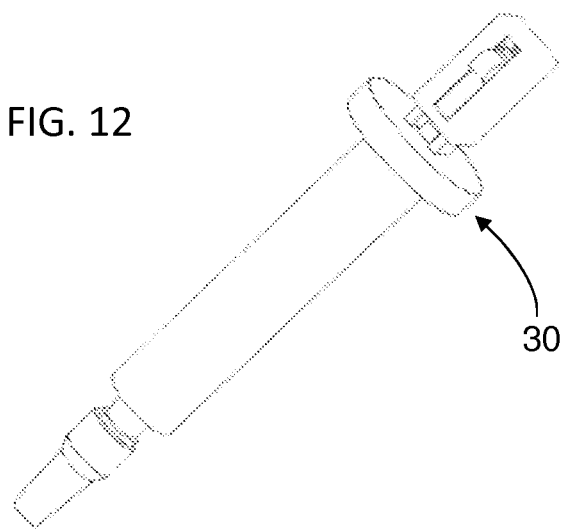
FIG. 12 is a perspective view of the second alternative injection assisting device assembled together with a pre-filled syringe having staked-needle according to the invention.
Figure 13:
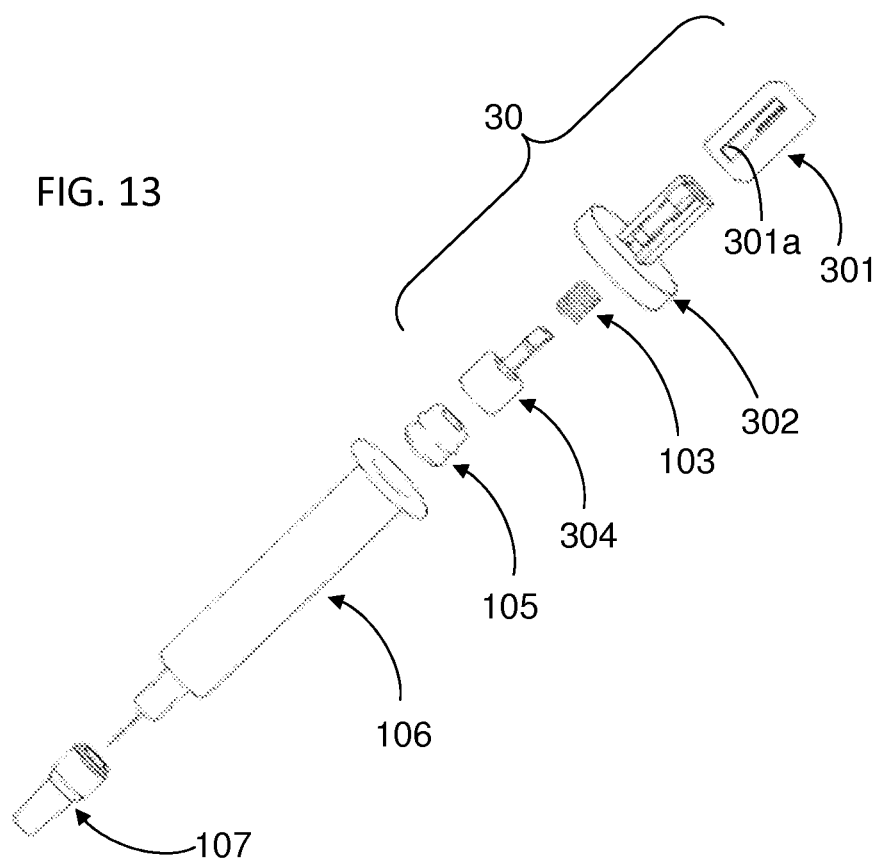
FIG. 13 is an exploded view of the second alternative injection assisting device assembled together with a pre-filled syringe having staked-needle according to the invention.

FIGS. 8-11 illustrate the first alternative injection assisting device assembly 20. In this exemplary injection assisting device assembly 20, a push cap 201 is used to activate an automatic injection. The push cap 201 is engaged with a connector 202, through guide keys 202a provided on the connector 102 and tracks 201a being defined on the push cap 201. This engagement prevents incidental activation of the device before use. During use, the push cap 201 is rotated to an activation position so that be push cap 201 can be pushed toward the distal end of the device. FIG. 10 shows the mounting of the pre-filled syringe on to the exemplary injection assisting device assembly 20. The connection between the exemplary injection device assembly 20 and the pre-filled syringe 11 is formed through a snap-fit feature 202d at the distal end of the connector 202 and the round flange 106b on the pre-filled syringe barrel 106. A latch lock mechanism is formed between a piston rod 204 and the connector 202. With reference to FIG. 11, the injection assisting device assembly 20 is shown with the piston rod 204 in a locked state. The piston rod 204 is restrained in the locked state, against biasing force of the spring 103, by deflectable latches formed between a feature 204a on the piston rod 204 and features 202c on the connector 202. The interengagement of the feature 204a and the features 202c restricts distal movement of the piston rod 204 under the biasing force of the spring 103. Upon activation, the push cap 201 is pushed toward the distal end of the device, a distally-directed tapered actuation surface 201b on the push cap 201 engages with outwardly tapered engagement surfaces 202b on the connector 202 and push features 202c on the connector 202 outward. Through the contact of engagement surfaces, a predetermined downward movement of the push cap 201 causes the outward movement of the restraining features 202c on the connector 202. The latch lock mechanism formed between the connector 202 and the piston rod 204 is released and the spring 103 drives the piston rod 204 to move toward the distal end of the device. The piston rod 204 pushes the piston 105 inside the pre-filled syringe 11 move toward the distal end of the pre-filled syringe 11. As the result, medication filled in the pre-filled syringe 11 is injected.

Figure 14:
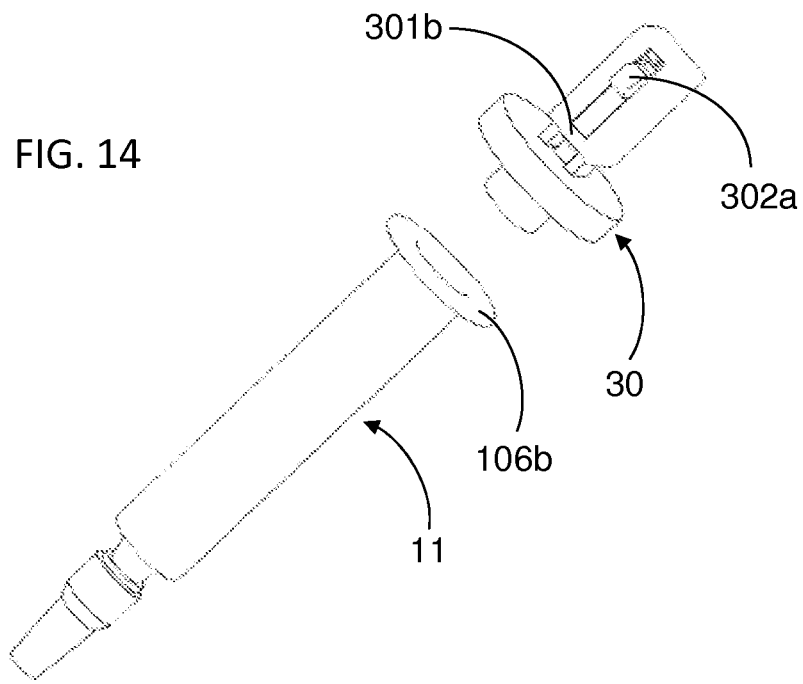
FIG. 14 is another exploded view of the assembling between the second alternative injection assisting device and a pre-filled syringe having staked-needle according to the invention.
Figure 15:
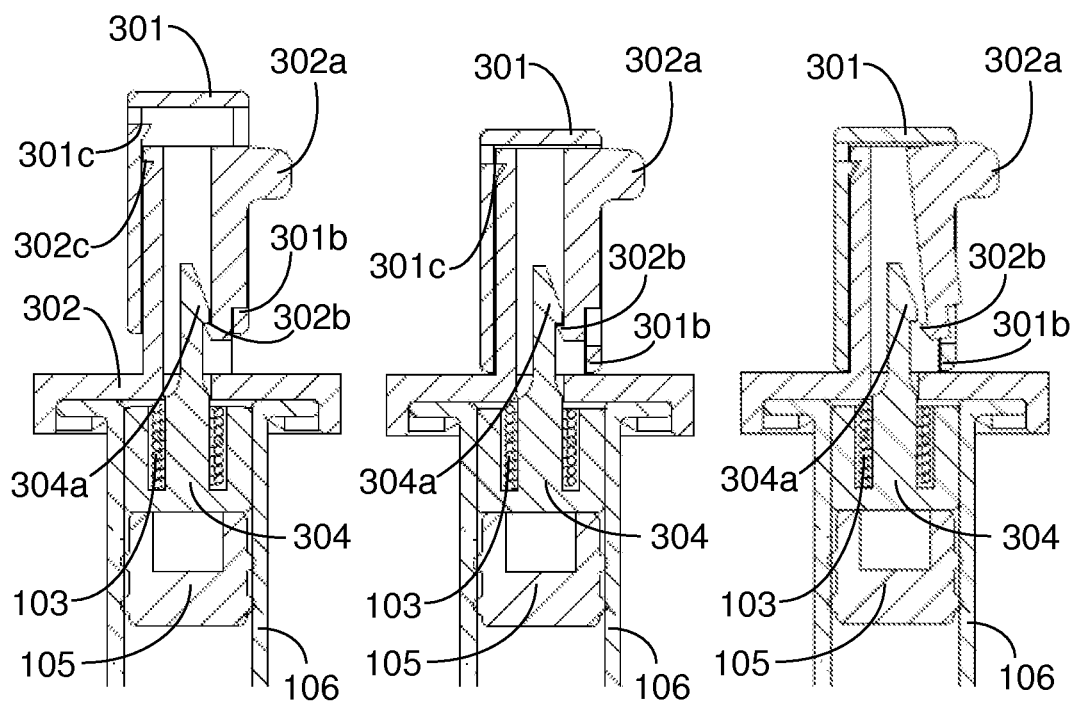
FIG. 15 shows a series of cross-sectional views of the activation the second alternative injection assisting device assembled together with a pre-filled syringe having staked-needle according to the invention.
Figure 16:
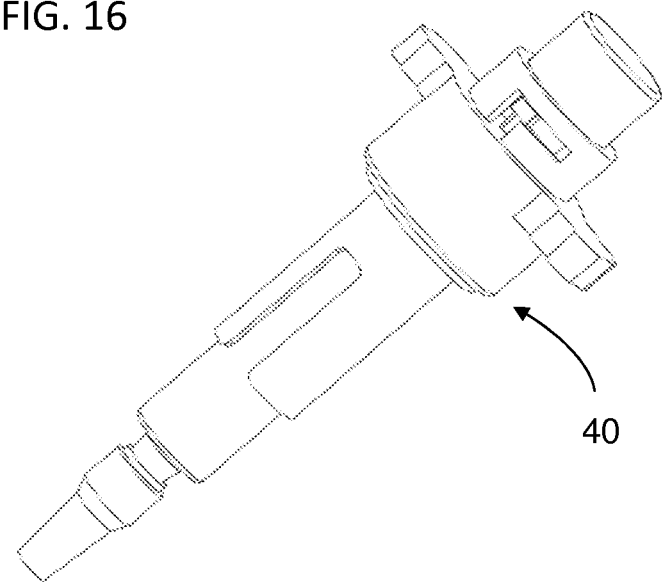
FIG. 16 is a perspective view of the third alternative injection assisting device assembled together with a pre-filled syringe having staked-needle according to the invention.
Figure 17:
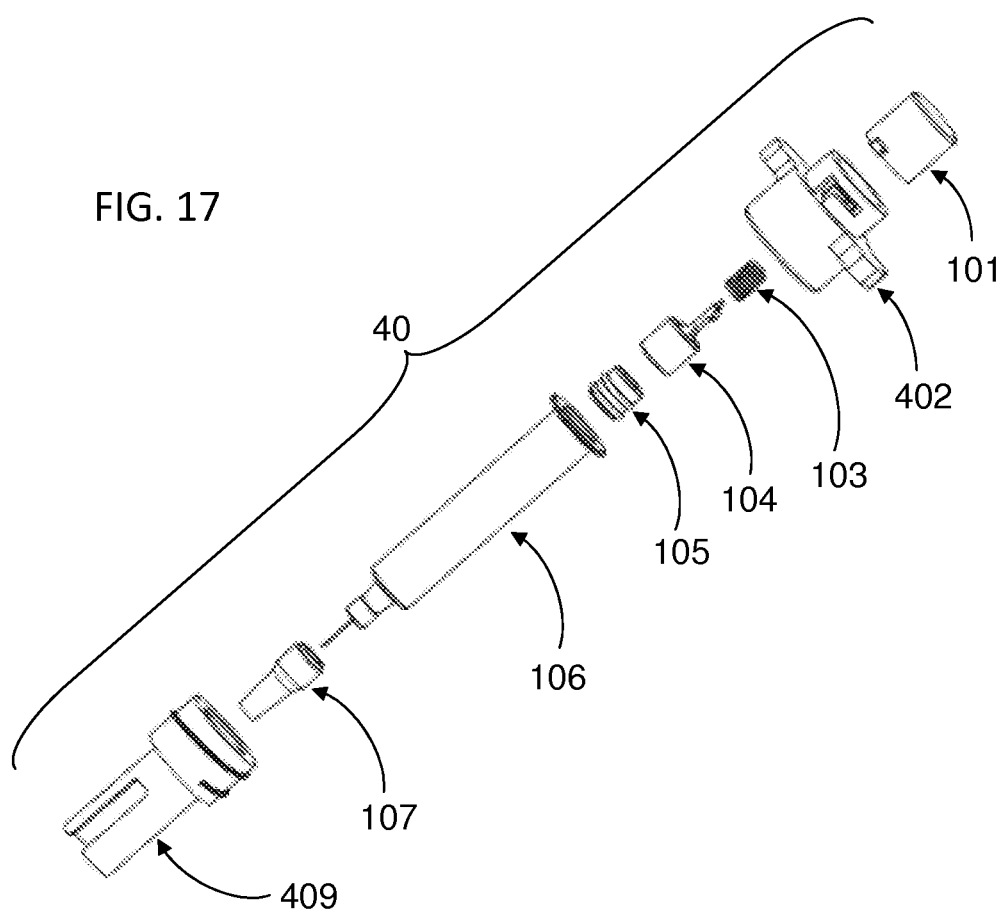
FIG. 17 is an exploded view of the third alternative injection assisting device assembled together with a pre-filled syringe having staked-needle according to the invention.

FIGS. 12-15 illustrate the second alternative injection assisting device assembly 30. In this exemplary injection assisting device assembly 30, a protection cap 301 is provided to protect an automatic injection activation mechanism defined within a connector 302. The protection cap 301 is engaged with the connector 302 through an activation button feature 302a provided on the connector 302 and a track 301a being defined on the protection cap 301. FIG. 14 shows the connection between the exemplary injection assisting device assembly 30 and the pre-filled syringe 11. The connection mechanism between the exemplary injection device assembly 30 and the pre-filled syringe 11 is the same as the injection device/syringe connection mechanism shown for the exemplary injection assisting device assembly 10. With reference to FIG. 15, a lock mechanism is formed between a piston rod 304 and the connector 302. Before activation, the piston rod 304 is restrained in the locked state, against biasing force of the spring 103, by a releasable locking mechanism formed between a locking finger feature 304a on the piston rod 304 and a locking finger feature 302b on the connector 302. A blocking feature 301b on the protection cap 301 blocks the movement of the locking finger feature 302b on the connector 302. This design prevents incidental activation of the device before use. During use, the protection cap 301 is pushed down toward to distal end of the device. A protrusion feature 301c on the protection cap 301 is engaged with a notch feature 302c on the connector 302. At the same time, the blocking feature 301b on the protection cap moves lower and frees the movement of the locking finger feature 302b on the connector 302 toward right. Then, the activation button 302a on the connector 302 is pushed toward left to activate the automatic injection. When the activation button 302a on the connector 302 is pushed toward left, the locking finger feature 302b on the connector moves toward right rotationally. As the result, the locking mechanism between the piston rod 304 and the connector 302 is released and the spring 103 drives the piston rod 304 to move toward the distal end of the device. The piston rod 304 pushes a piston 105 inside the pre-filled syringe 11 move toward the distal end of the pre-filled syringe 11. Consequently, medication filled in the pre-filled syringe 11 is injected.

Figure 18:
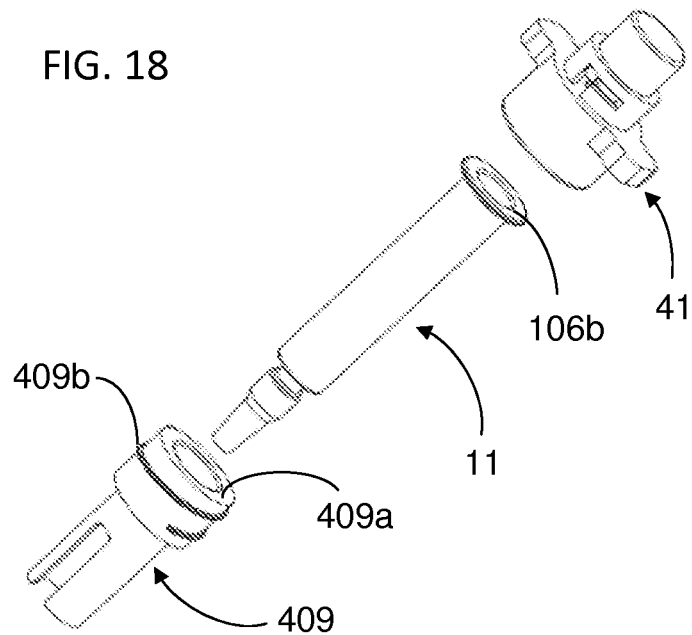
FIG. 18 is another exploded view of the assembling between the third alternative injection assisting device and a pre-filled syringe having staked-needle according to the invention.
Figure 19:
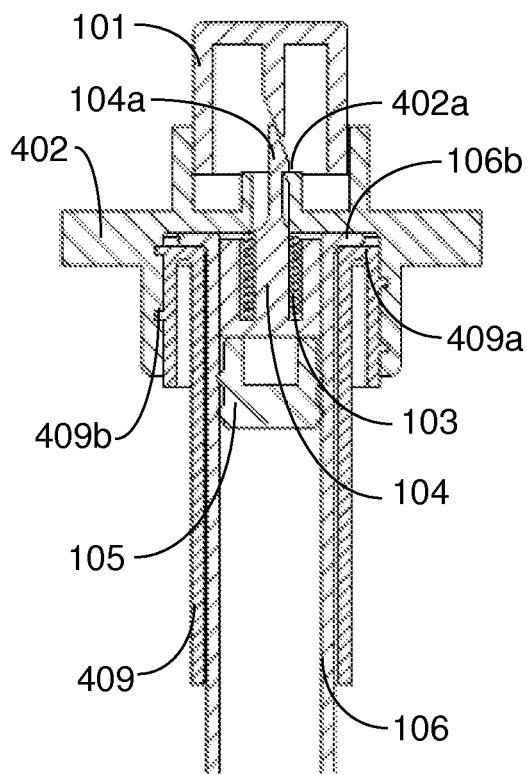
FIG. 19 is a cross-sectional view showing mounting a pre-filled syringe having staked-needle on the third alternative injection assisting device according to the invention.
Figure 20:
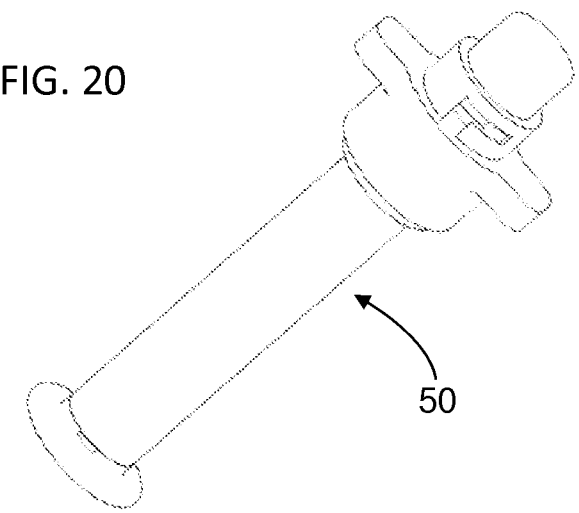
FIG. 20 is a perspective view of the fourth alternative injection assisting device assembled together with a pre-filled syringe having staked-needle according to the invention.
Figure 21:
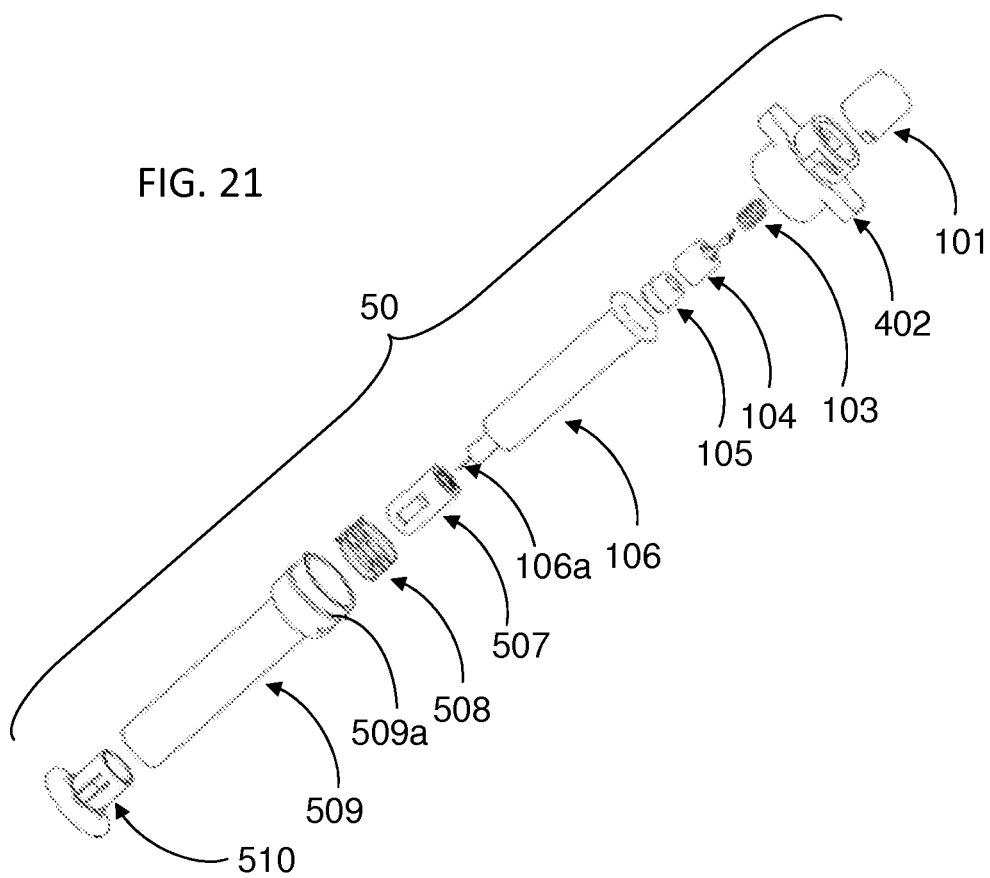
FIG. 21 is an exploded view of the fourth alternative injection assisting device assembled together with a pre-filled syringe having staked-needle according to the invention.

FIGS. 16-19 illustrate the third alternative injection assisting device assembly 40. In this exemplary injection assisting device assembly 40, the push cap 101 is used to activate an automatic injection. The push cap 101 is engaged with a connector 402. With reference to FIGS. 18 and 19, the connection between the exemplary injection device assembly 40 and the pre-filled syringe 11 is through an engagement between a sub-assembly 41 (formed by the push cap 101, the connector 402, the piston rod 104 and the spring 103) and a sheath 409. To mount the pre-filled syringe 11 on the exemplary injection assisting device assembly 40, the pre-filled syringe 11 is first inserted in the sheath 409 and the flange 106b of the pre-filled syringe 11 is landed on a surface 409a on the sheath 409. Then, the sheath 409 together with the pre-filled syringe 11 is assembled with a sub-assembly 41 through a thread engagement. A thread feature 409b on the sheath 409 is shown in the FIGS. 18 and 19. After the thread feature 409b is fully engaged, the flange 106b on the pre-filled syringe 11 is restrained between the sheath 409 and the connector 402. The automatic injection activation mechanism of the third alternative injection assisting device assembly 40 is the same as the automatic injection activation mechanism of the exemplary injection assisting device assembly 10. When the push cap 101 is pushed toward the distal end of the injection device, the releasable latch lock mechanism, formed between the feature 104a on the piston rod 104 and a feature 402a on the connector 402, is released. Then, the piston rod 104 pushes the piston 105 inside the pre-filled syringe barrel 106 move toward the distal end of the pre-filled syringe 11. As the result, medication filled in the pre-filled syringe 11 is injected.

Figure 22:
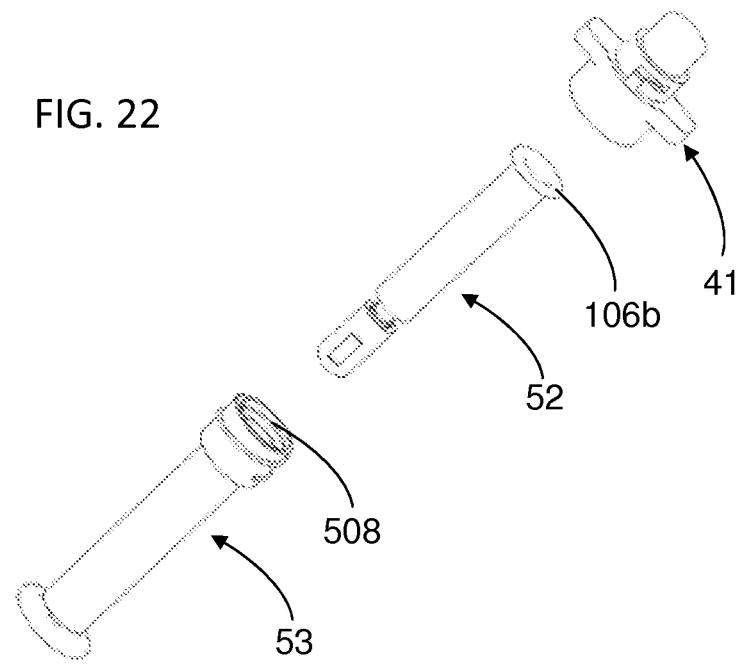
FIG. 22 is another exploded view of the assembling between the fourth alternative injection assisting device and a pre-filled syringe having staked-needle according to the invention.
Figure 23:
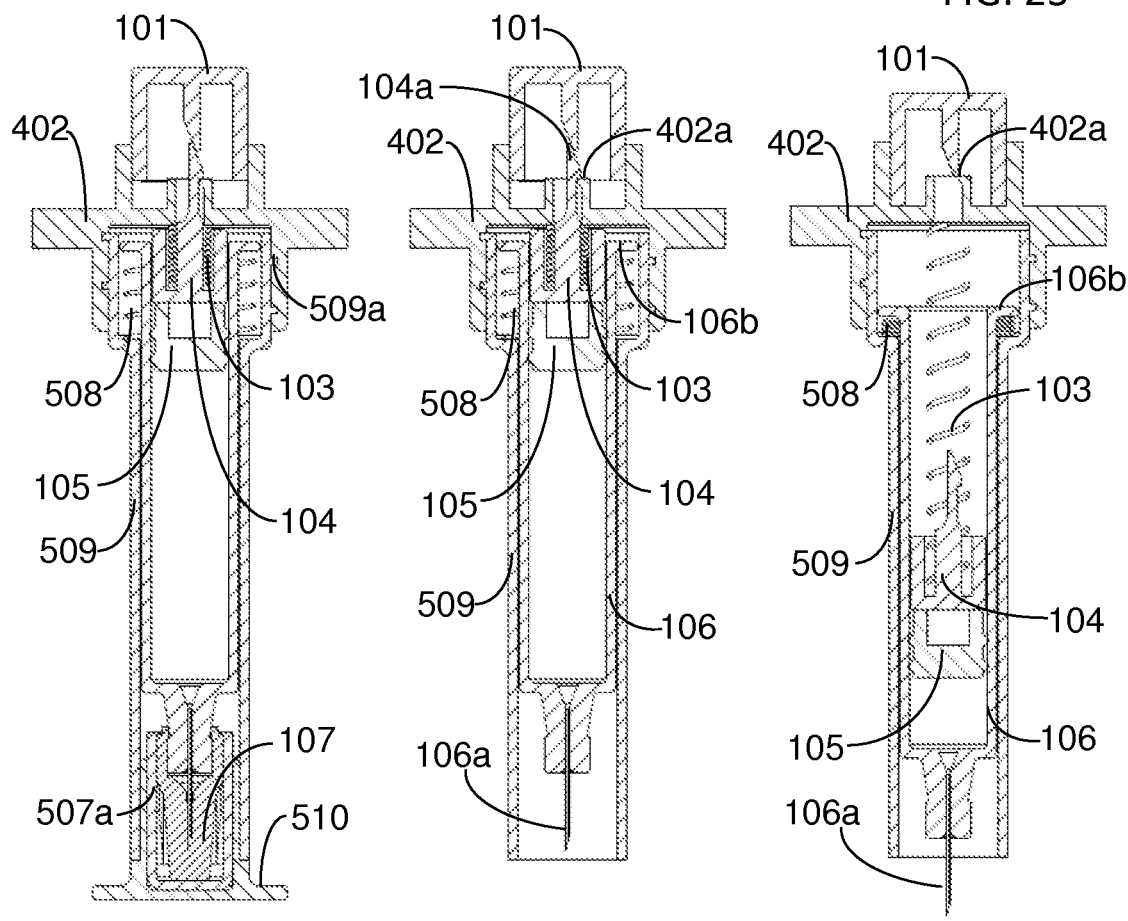
FIG. 23 shows a series of cross-sectional views of the activation the fourth alternative injection assisting device assembled together with a pre-filled syringe having staked-needle according to the invention.

FIGS. 20-23 illustrate the fourth alternative injection device assembly 50. In this exemplary injection device assembly 50, the push cap 101 is used to activate an automatic injection. The push cap 101 is engaged with the connector 402. With reference to FIGS. 22 and 23, the connection between the fourth alternative injection device assembly 50 and a pre-filled syringe 52 is through an engagement between the sub-assembly 41 and a sheath sub-assembly 53. A pre-filled syringe 52 comprises the syringe barrel 106 with staked needle 106a and a needle shield sub-assembly 507, which is formed by the needle shield 107 and a rigid needle shield 507a. The sheath sub-assembly 53 is formed by a sheath 509, a supporting spring 508 and a needle shield puller 510. To mount the pre-filled syringe 52 with the exemplary injection assisting device 50, the pre-filled syringe 52 is first inserted into the sheath sub-assembly 53. The flange 106b of the pre-filled syringe 52 is landed on the supporting spring 508 being housed in the sheath 509. The needle shield sub-assembly 507 is engaged with the needle shield puller 510. The engagements between a needle shield and a needle shield removing mechanism are common. So, details of the engagement between needle shield sub-assembly 507 and needle shield puller 510 aren't discussed herein. The sheath sub-assembly 53 together with the pre-filled syringe 52 is assembled with the sub-assembly 41 through thread engagement. A thread feature 509a on the sheath 509 is shown in the FIGS. 22 and 23. After the thread feature 509a is fully engaged, the flange 106b is restrained between the supporting spring 508 and the connector 402. Before injection, the needle shield sub-assembly 507 is removed by pulling the needle shield puller 510 down. The automatic injection activation mechanism of the fourth alternative injection device assembly 40 is the same as the automatic injection activation mechanism of the exemplary injection assisting device assembly 10. When the push cap 101 is pushed toward the distal end of the injection assisting device, the releasable latch lock mechanism, formed between the feature 104a on the piston rod 104 and the feature 402a on the connector 402, is released, and the piston rod 104 pushes the piston 105 inside the pre-filled syringe barrel 106 move toward the distal end of the pre-filled syringe 52. As the result, medication filled in the pre-filled syringe 52 is injected. Furthermore, because of the hydraulic resistant generated by the medication inside the syringe barrel 106 during injection, the spring force generated by the spring 103 also pushes the syringe barrel 106 together with the staked needle 106a toward the distal end of the device. Consequently, the supporting spring 508 is compressed and the staked needle 106a is inserted into injection site for medication injection.

All the features in the above embodiments and design concepts herein can be inter-changed and combined to generate new device designs. Those of skill in the art will understand that modifications (additions and/or removals) of various components of the apparatuses, methods and/or systems and embodiments described herein may be made without departing from the full scope and spirit of the present invention, which encompass such modifications and any and all equivalents thereof.

The invention claimed is:

1. A device for medication injection comprising:
   a syringe having an internal surface defining an interior chamber, a distal end and a proximal end, wherein said distal end of said syringe is distally tapered to form a conical shaped projection and said proximal end of said syringe having an outward flange shaped projection;
   a connector having a distal end and a proximal end, wherein said proximal end of said syringe is disposed between said distal end of said connector and said proximal end of said connector;
   a piston rod having a distal end and locked with said connector before medication injection;
   a resilient member disposed inside of said interior chamber of said syringe, said resilient member having a proximal end proximate said proximal end of said syringe and a distal end proximate said distal end of said piston rod, wherein said resilient member is contacting and biasing against said connector, and configured to bias said piston rod distally; and
   a restraining means configured to restrain said piston rod against biasing of said resilient member.

2. The device for medication injection as in claim 1, wherein said syringe is displaceable distally.

3. The device for medication injection as in claim 2, further comprising a supporting spring to bias against said syringe to move distally.

4. The device for medication injection as in claim 1, wherein said syringe having a needle disposed at said distal end.

5. The device for medication injection as in claim 4, further comprising a sheath to hide said needle before injection.

6. The device for medication injection as in claim 1, wherein said connector having a means for finger gripping.

7. The device for medication injection as in claim 1, further comprising a means for preventing incidental releasing of said restraining means.

8. The device for medication injection as in claim 1, wherein said syringe having a luer fitting disposed at said distal end.

* * * * *